United States Patent
Dhawan et al.

(10) Patent No.: US 10,928,773 B2
(45) Date of Patent: Feb. 23, 2021

(54) HOLOGRAPHIC IMAGE REPLICATION

(71) Applicant: INTERNATIONAL BUSINESS MACHINES CORPORATION, Armonk, NY (US)

(72) Inventors: Vinay Dhawan, Noida (IN); Siddharth Saraya, Raniganj (IN); Deepak Gupta, Indirapuram (IN)

(73) Assignee: International Business Machines Corporation, Armonk, NY (US)

( * ) Notice: Subject to any disclaimer, the term of this patent is extended or adjusted under 35 U.S.C. 154(b) by 5 days.

(21) Appl. No.: 16/178,064

(22) Filed: Nov. 1, 2018

(65) Prior Publication Data
US 2020/0142354 A1 May 7, 2020

(51) Int. Cl.
*G03H 1/00* (2006.01)
*G03H 1/22* (2006.01)

(52) U.S. Cl.
CPC .............. *G03H 1/0005* (2013.01); *G03H 1/22* (2013.01); *G03H 2001/0088* (2013.01); *G03H 2210/30* (2013.01); *G03H 2226/02* (2013.01)

(58) Field of Classification Search
CPC .... G03H 1/0005; G03H 1/22; G03H 2226/02; G03H 2210/30; G03H 2001/0088
See application file for complete search history.

(56) References Cited

U.S. PATENT DOCUMENTS

| | | | |
|---|---|---|---|
| 8,072,488 B2 | 12/2011 | Cable et al. | |
| 8,395,657 B2 | 3/2013 | Jacob | |
| 9,562,761 B2 | 2/2017 | Takai | |
| 9,661,272 B1 | 5/2017 | Daniel | |
| 9,770,217 B2 | 9/2017 | Sandholm | |
| 2014/0071229 A1 | 3/2014 | Weerasinghe | |
| 2014/0176661 A1 | 6/2014 | Smurro | |

(Continued)

OTHER PUBLICATIONS

Accenture Technology; Mixed Reality Brings Real Benefits to Enterprises; https://www.accenture.com/_acnmedia/Accenture/Conversion-Assets/DotCom/Documents/Global/PDF/Industries_19/Accenture-Mixed-Reality-POV-Final.pdf; retrieved from the Internet Apr. 12, 2018; 16 pages.

(Continued)

*Primary Examiner* — James M Pontius
(74) *Attorney, Agent, or Firm* — Schmeiser, Olsen & Watts; William H. Hartwell

(57) ABSTRACT

A method and system for improving holographic image simulation and replication is provided. The method includes receiving data identifying a primary location and at least one secondary location associated with a holographic replication event. First video data describing first objects at the primary location is received and a first holographic simulation presentation comprising virtual representations of the first objects is generated. Second video data describing second objects at the at least one secondary location is received and a second holographic simulation presentation comprising virtual representations of the second objects is generated. The second holographic simulation presentation is projected such that said virtual representations of the second objects interact with the first objects at the primary location. The first holographic simulation presentation is projected such that said virtual representations of the first objects interact with the second objects at the at least one secondary location.

18 Claims, 7 Drawing Sheets

(56) References Cited

U.S. PATENT DOCUMENTS

2017/0248915 A1 8/2017 Oh
2019/0313059 A1* 10/2019 Agarawala .............. G06T 19/20

OTHER PUBLICATIONS

Sayawat, Nina; Holoportation Takes Virtual Reality Meetings to the Next Level; Smart Meetings; https://www.smartmeetings.com/technology/86582/holoportation-for-virtual-reality-meetings; Mar. 30, 2016; 7 pages.

* cited by examiner

HOLOGRAPHIC IMAGE REPLICATION

FIELD

The present invention relates generally to a method for generating a holographic image simulation and in particular to a method and associated system for improving holographic image technology associated with generating interactive holographic image simulation replications for real time interactions with individuals.

BACKGROUND

Accurately simulating visual data typically includes an inaccurate process with little flexibility. Communicating visual data with multiple remote parties may include a complicated process that may be time consuming and require a large amount of resources. Accordingly, there exists a need in the art to overcome at least some of the deficiencies and limitations described herein above.

SUMMARY

A first aspect of the invention provides a holographic image simulation and replication improvement method comprising: receiving, by a processor of a holographic image generation device, data identifying a first location and at least one secondary location associated with a holographic replication event; continuously receiving in real time, by the processor via a plurality of sensors at the first location, first video data describing first objects at the first location; continuously generating in real time, by the processor based on the first video data, a first holographic simulation presentation comprising virtual representations of the first objects with respect to the first location; continuously receiving in real time, by the processor via a plurality of sensors at the at least one secondary location, second video data describing second objects at the second location; continuously generating in real time, by the processor based on the second video data, a second holographic simulation presentation comprising virtual representations of the second objects with respect to the second location; continuously projecting in real time, by the processor at the first location, the second holographic simulation presentation such that the virtual representations of the second objects overlay and interact with the first objects at the first location; and continuously projecting in real time, by the processor at the second location, the first holographic simulation presentation such that the virtual representations of the first objects overlay and interact with the second objects at the second location.

A second aspect of the invention provides a computer program product, comprising a computer readable hardware storage device storing a computer readable program code, the computer readable program code comprising an algorithm that when executed by a processor of a holographic image generation device implements a holographic image simulation and replication improvement method, the method comprising: receiving, by the processor, data identifying a first location and at least one secondary location associated with a holographic replication event; continuously receiving in real time, by the processor via a plurality of sensors at the first location, first video data describing first objects at the first location; continuously generating in real time, by the processor based on the first video data, a first holographic simulation presentation comprising virtual representations of the first objects with respect to the first location; continuously receiving in real time, by the processor via a plurality of sensors at the at least one secondary location, second video data describing second objects at the second location; continuously generating in real time, by the processor based on the second video data, a second holographic simulation presentation comprising virtual representations of the second objects with respect to the second location; continuously projecting in real time, by the processor at the first location, the second holographic simulation presentation such that the virtual representations of the second objects overlay and interact with the first objects at the first location; and continuously projecting in real time, by the processor at the second location, the first holographic simulation presentation such that the virtual representations of the first objects overlay and interact with the second objects at the second location.

A third aspect of the invention provides a holographic image generation device comprising a processor coupled to a computer-readable memory unit, the memory unit comprising instructions that when executed by the processor implements a holographic image simulation and replication improvement method comprising: receiving, by the processor, data identifying a first location and at least one secondary location associated with a holographic replication event; continuously receiving in real time, by the processor via a plurality of sensors at the first location, first video data describing first objects at the first location; continuously generating in real time, by the processor based on the first video data, a first holographic simulation presentation comprising virtual representations of the first objects with respect to the first location; continuously receiving in real time, by the processor via a plurality of sensors at the at least one secondary location, second video data describing second objects at the second location; continuously generating in real time, by the processor based on the second video data, a second holographic simulation presentation comprising virtual representations of the second objects with respect to the second location; continuously projecting in real time, by the processor at the first location, the second holographic simulation presentation such that the virtual representations of the second objects overlay and interact with the first objects at the first location; and continuously projecting in real time, by the processor at the second location, the first holographic simulation presentation such that the virtual representations of the first objects overlay and interact with the second objects at the second location.

The present invention advantageously provides a simple method and associated system capable of accurately simulating visual data.

BRIEF DESCRIPTION OF THE DRAWINGS

FIG. 4, including

DETAILED DESCRIPTION

Figure 1:
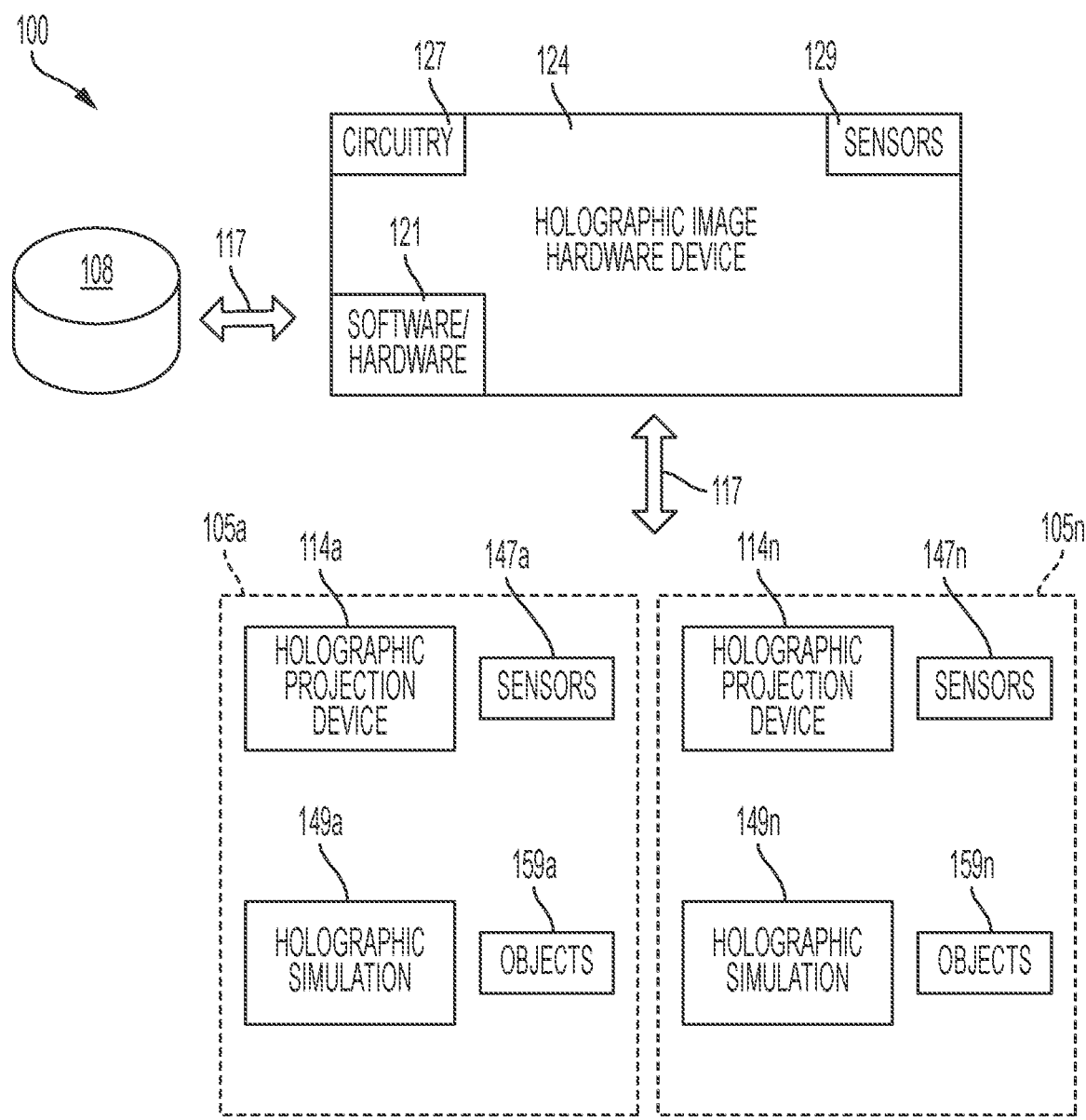
FIG. 1 illustrates a holographic simulation system for improving holographic image technology associated with generating interactive holographic image simulation replications for real time interactions with individuals, in accordance with embodiments of the present invention.

FIG. 1 illustrates a holographic simulation system 100 for improving holographic image technology associated with generating interactive holographic image simulation replications for real time interactions with individuals, in accordance with embodiments of the present invention. System 100 enables a holographic image hardware device 124 for executing a process for dynamically and holographically stitching objects (human or inanimate) at different locations (e.g., locations 105a . . . 105n) and replicating movement and action of real objects and virtual objects at the different locations to present an entire visual scenario to all users. The process includes: enabling cameras for visually replicating objects (e.g., objects 159a . . . 159n of FIG. 1) by recording the objects from various angles and dimensions for reproducing a 3-dimensional holographic image (or simulation such as holographic simulation 149a . . . 149n) of the objects. In response, holographic objects are generated at all associated locations. The process involves a primary location and a secondary(s) location. All objects (including movements and actions) located within a defined boundary of the primary location are replicated (holographically) at all secondary locations. Likewise, all objects (including movements and actions) located within a defined boundary of the secondary location(s) are replicated (holographically) at the primary location.

The aforementioned process enables a user to simulate all objects and associated actions (in real time) across multiple locations. Therefore, integration of objects between multiple locations allows for creating of a scenario for users to look and follow. For example, the process may be used in emergency situations to guide even a user to follow actions being implemented via a virtual holographic object.

System 100 of FIG. 1 includes a holographic image hardware device 124 (i.e., specialized hardware device), a holographic projection device 114a (and associated sensors 147a at a location 105a), a holographic projection device 114n (and associated sensors 147n at a location 105n), and a database 108 (e.g., a cloud-based system) interconnected through a network 117. System 100 enables a process for generating a holographic image simulation (e.g., holographic simulations 149a . . . 149n). Holographic image hardware device 124 includes specialized circuitry 127 (that may include specialized software), software code/hardware structure 121 (i.e., including self-learning software code), and sensors 129. Sensors 129 may include any type of internal or external sensor (or biometric sensor) including, inter alia, a heart rate monitor, a blood pressure monitor, a temperature sensor, a pulse rate monitor, an ultrasonic sensor, an optical sensor, a video retrieval device, an audio retrieval device, humidity sensors, ultrasonic transducers, a heatmap sensor, etc. Holographic projection device 114a (including sensors 147a) may include a stationary projection device or a mobile projection device including a vehicular projection device. A vehicular projection device may include any type of vehicle that does not require a human operator to be located within the vehicle such as, inter alia, a remote controlled vehicle (e.g., an aircraft flown by a pilot at a ground control station), an autonomously controlled vehicle (e.g., an aircraft controlled based on pre-programmed flight plans and may include an intelligence algorithm that would enable the vehicle to know it's location and self-determine a holographic projection location), a pre-programmed vehicle, etc. Alternatively, the vehicle may comprise any type of vehicle that includes a human operator located within the vehicle (e.g., an aircraft, an automobile, a boat or ship, a train, etc.). The vehicles may include, inter alia, an aerial vehicle, a land based vehicle, a marine (water) based vehicle, etc. Sensors 147a may include a video retrieval device, an audio retrieval device, a heatmap sensor, an optical sensor, and an ultrasonic sensor, etc. Holographic projection device 114n (including sensors 147n) may include a stationary projection device or a mobile projection device including a vehicular projection device. Sensors 147n may include a video retrieval device, an audio retrieval device, a heatmap sensor, an optical sensor, and an ultrasonic sensor, etc. Holographic image hardware device 124, holographic projection device 114a, holographic projection device 114n, and database 108 may each may comprise an embedded device. An embedded device is defined herein as a dedicated device or computer comprising a combination of computer hardware and software (fixed in capability or programmable) specifically designed for executing a specialized function. Programmable embedded computers or devices may comprise specialized programming interfaces. In one embodiment, holographic image hardware device 124, holographic projection device 104a, holographic projection device 114n, and database 108 may each comprise a specialized hardware device comprising specialized (non-generic) hardware and circuitry (i.e., specialized discrete non-generic analog, digital, and logic-based circuitry) for (independently or in combination) executing a process described with respect to FIGS. 1-6. The specialized discrete non-generic analog, digital, and logic-based circuitry may include proprietary specially designed components (e.g., a specialized integrated circuit, such as for example an Application Specific Integrated Circuit (ASIC) designed for only implementing an automated process for improving holographic image technology associated with generating interactive holographic image simulation replications for real time interactions with individuals. Network 117 may include any type of network including, inter alia, a local area network, (LAN), a wide area network (WAN), the Internet, a wireless network, etc. Alternatively, network 117 may include an application programming interface (API). System 100 enables a process for generating a holographic image simulation as follows:

The process is initiated when locations to be stitched together are identified. In response, installed video retrieval devices are enabled for viewing objects and associated actions within the locations. The video retrieval devices capture images such that basic learning attributes (for standard objects) are pre-captured with the system and preconfigured code is used for identifying the objects at a location.

Visual replications of the objects may be captured from various angles such that a 3-dimensional view of the object is generated thereby creating a database of 3 dimensional objects for use in holographic image projection. Additionally, multiple images (from multiple locations) are identified for stitching and one location is designated as a primary location and all additional locations are designated as secondary locations. When a user a selects a primary location, a request for defining a region within an entire space of the primary location is generated. The user may select an entire (object) image retrieved by a camera within the primary location and in response, the entire image is projected at the secondary locations via usage of a holographic projector. Each object image is projected separately such that primary person may perform actions associated with the object images. Likewise, participating objects from secondary locations are identified and selected and in response, selected objects and associated locations are captured and replicated at the primary location. Therefore, when an object identified at secondary locations moves or performs any action, an associated holographic image is replicated at the primary location thereby allowing holographic replications at all locations for instructional purposes. The following implementation example describes an implementation process executed by system 100:

The process is associated with a medical procedure taking place at a primary location within a country A under the supervision of a senior physician from a secondary location within a country B. System 100 is configured to learn objects representing various instruments, assistants, and physicians at the both the primary and secondary locations. Cameras located at the primary and secondary locations are enabled to capture real time movement of the objects (i.e., devices and people present). The primary location includes an examination room designated as a space for replication. Therefore, the examination room (and all objects within the examination room) is virtually replicated as a holographic simulation for presentation at the secondary location. Additionally, a first physician at the secondary location is selected for display at the primary location resulting in a holographic simulation presentation (at the secondary location) comprising holographic objects surrounding the first physician. Likewise, users at the primary location are able to view the first physician as if he/she were in the same room. Subsequently (as the first physician moves an associated holographic image), a second physician at the primary location replicates a same action in real time. Therefore, if the second physician picks up any of the holographic objects, all individuals at the primary location are able to view a replication of the associated holographic object and an associated action. Similarly, at secondary location, the first physician is able to view all object movements and associated actions at the primary location. For example, with respect to an examination table surrounded by physicians at the primary location, the first physician may view all virtual holographic objects surrounding him/her as if he/she were located at the primary location. Therefore, when the first physician picks up the virtual holographic object and performs an action (e.g., picks up a virtual scapula and makes an incision on a virtual patient, all physicians at the primary location are able to view the action via a holographic image of the secondary physician performing the action thereby instructing (i.e., providing guidance) the primary physician with respect to the specified procedure. Additionally, holographic images of all physicians comprise audible functionality for providing verbal instructions.

System 100 is configured to execute processes associated with additional implementation examples as follows: For example, a customer support representative may activate virtual holographic images for replicating a space for directing a user to an exact location on a monitor or to a part to be repaired.

Figure 2:
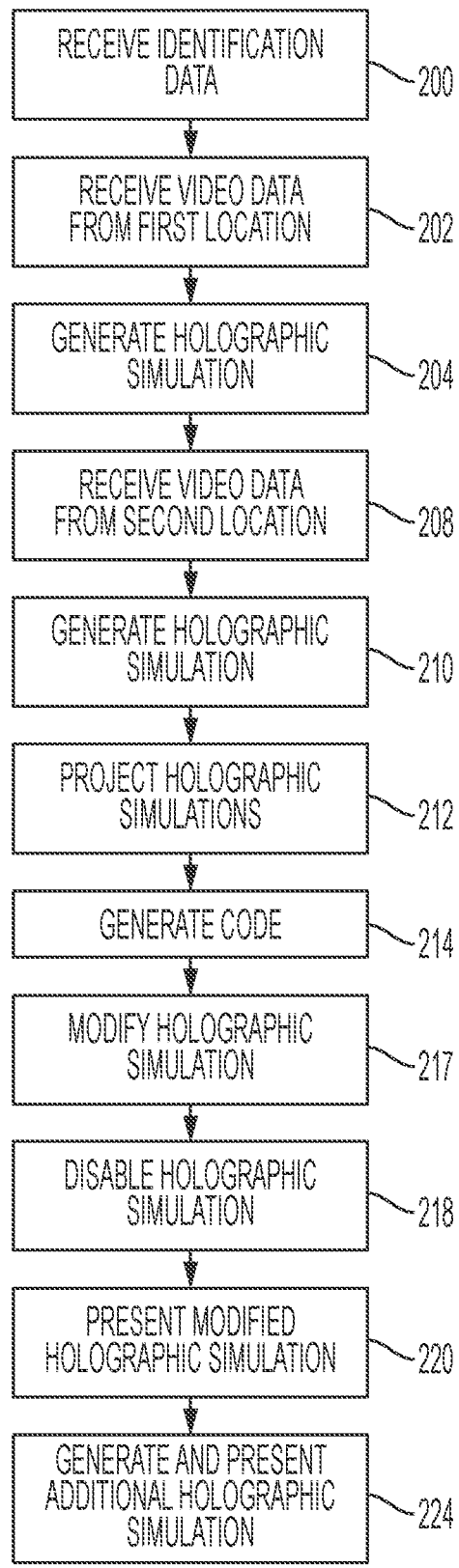
FIG. 2 illustrates an algorithm detailing a process flow enabled by the system of FIG. 1 for improving holographic image technology associated with generating interactive holographic image simulation replications for real time interactions with individuals, in accordance with embodiments of the present invention.

FIG. 2 illustrates an algorithm detailing a process flow enabled by system 100 of FIG. 1 for improving holographic image technology associated with generating interactive holographic image simulation replications for real time interactions with individuals, in accordance with embodiments of the present invention. Each of the steps in the algorithm of FIG. 2 may be enabled and executed in any order by a computer processor(s) executing computer code. Additionally, each of the steps in the algorithm of FIG. 2 may be enabled and executed in combination by holographic image hardware device 124, holographic projection device 114a . . . 114n, and database 108. In step 200, data identifying a primary location and a secondary location associated with a holographic replication event is received by a holographic image generation device. In step 202, first video data describing first objects at the primary location is continuously received (in real time via sensors (e.g., a video retrieval device, an audio retrieval device, a heatmap sensor, an optical sensor, an ultrasonic sensor, etc.) at the primary location). The first video data may describe a shape, a three-dimensional size, and a relative position of each of the first objects with respect to said primary location. The first objects may include inanimate objects and living objects. In step 204, a first holographic simulation presentation including virtual representations of the first objects with respect to the primary location are continuously generated in real time based on the first video data. The virtual representations of the first objects may execute replicated virtual movements simultaneously with actual movements of the first objects. In step 208, second video data describing second objects at the secondary location is continuously received (in real time via sensors (e.g., a video retrieval device, an audio retrieval device, a heatmap sensor, an optical sensor, an ultrasonic sensor, etc.) at the secondary location). The second video data may describe a shape, a three-dimensional size, and a relative position of each of the second objects with respect to the secondary location. The second objects may include inanimate objects and living objects. In step 210, a second holographic simulation presentation including virtual representations of the second objects with respect to the secondary location are continuously generated in real time based on the second video data. The virtual representations of the second objects may execute replicated virtual movements simultaneously with actual movements of the second objects. In step 212, the second holographic simulation presentation is continuously projected (in real time) such that the virtual representations of the second objects overlay and interact with the first objects at the primary location. Likewise, the second holographic simulation presentation is continuously projected (in real time) such that the virtual representations of the second objects overlay and interact with the first objects at the primary location. Continuously projecting the first holographic simulation presentation and the second holographic simulation presentation may occur simultaneously. Projecting the first holographic simulation presentation may include projecting the virtual representations of the second objects interacting with the first objects at a speed that is equal to, less than, or greater than a real time speed of the second objects. Likewise, projecting the second holographic simulation presentation comprises projecting the virtual representations of the first objects interacting with the second objects at a speed that is equal to, less than, or greater than a real time speed of the first objects.

In step 214, self-learning software code for executing future holographic simulation presentations is generated based on the first holographic simulation presentation and the second holographic simulation presentation. In step 217, the first and/or second holographic simulation presentation is modified (based on retrieved feedback data resulting from execution of the self-learning software code) such that a modified holographic simulation presentation is generated. In step 218, the first and/or second holographic simulation presentation is disabled. In step 220, the modified holographic simulation presentation is continuously projected in real time such that virtual representations of the multiple objects overlay and interact with objects at the primary location and the secondary location. In step 224, an additional holographic simulation is generated and projected in combination with the first, second and/or modified holographic simulation.

Figure 3:
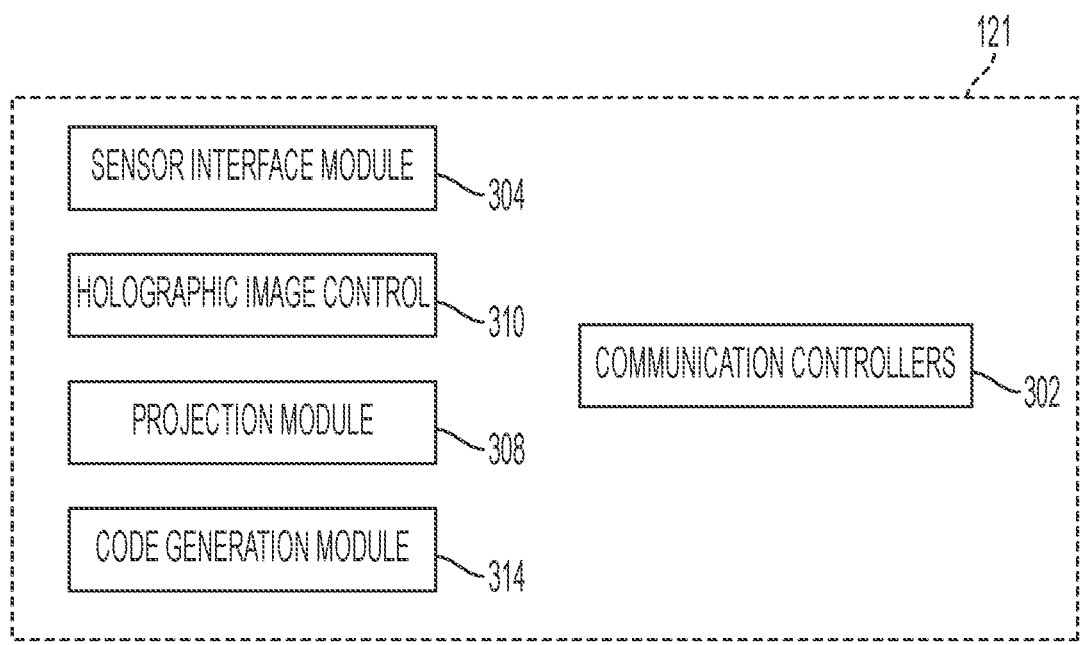
FIG. 3 illustrates an internal structural view of the software/hardware structure of FIG. 1, in accordance with embodiments of the present invention.

FIG. 3 illustrates an internal structural view of software/hardware structure 121 of FIG. 1, in accordance with embodiments of the present invention. Software/hardware structure 121 includes a sensor interface module 304, a holographic image control module 310, a projection module 308, a code generation module 314, and communication controllers 302. Sensor interface module 304 comprises specialized hardware and software for controlling all functions related to sensors 129 and sensors 147a . . . 147n of FIG. 1. Holographic image control module 310 comprises specialized hardware and software for controlling all functionality related to generating specified holographic images as described with respect to the algorithm of FIG. 2. Projection module 308 comprises specialized hardware and software for controlling all functions related to a holographic projector projecting specified holographic images as described with respect to the algorithm of FIG. 2. Code generation module 314 comprises specialized hardware and software for controlling all functions related to and generating self-learning software code for executing future holographic simulation processes. Communication controllers 302 are enabled for controlling all communications between sensor interface module 304, holographic image control module 310, presentation module 308, and code generation module 314.

Figure 4A:
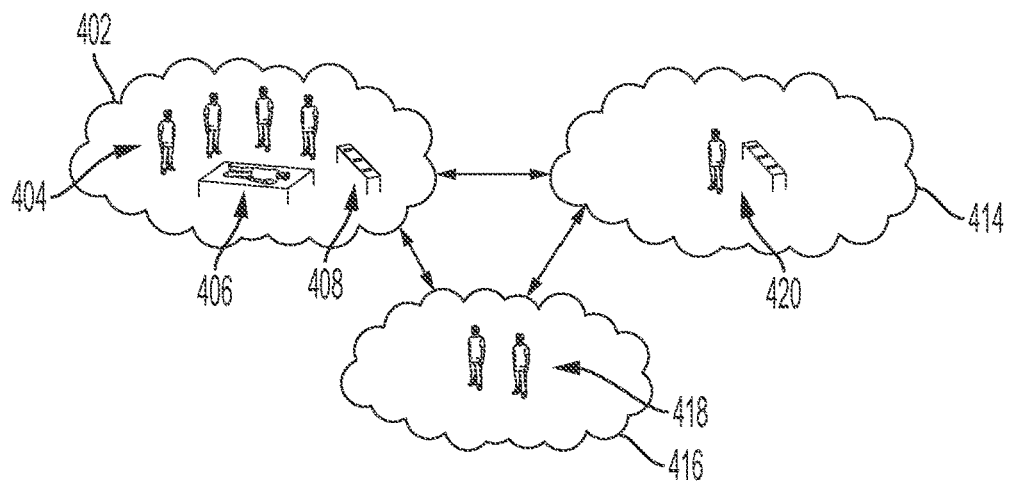
FIGS. 4A-4C, illustrates a medical procedure based implementation example executed by the system of FIG. 1 for improving holographic image technology associated with generating interactive holographic image simulation replications for real time interactions with individuals, in accordance with embodiments of the present invention
Figure 4B:
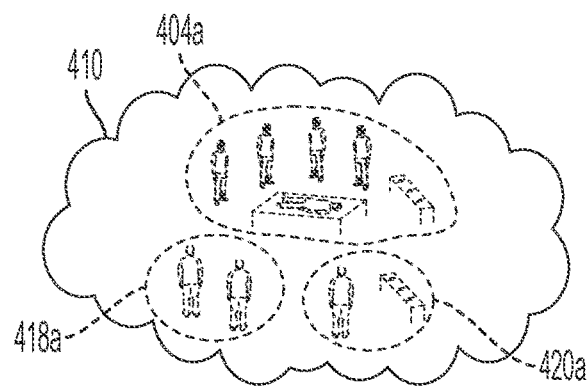
Figure 4C:
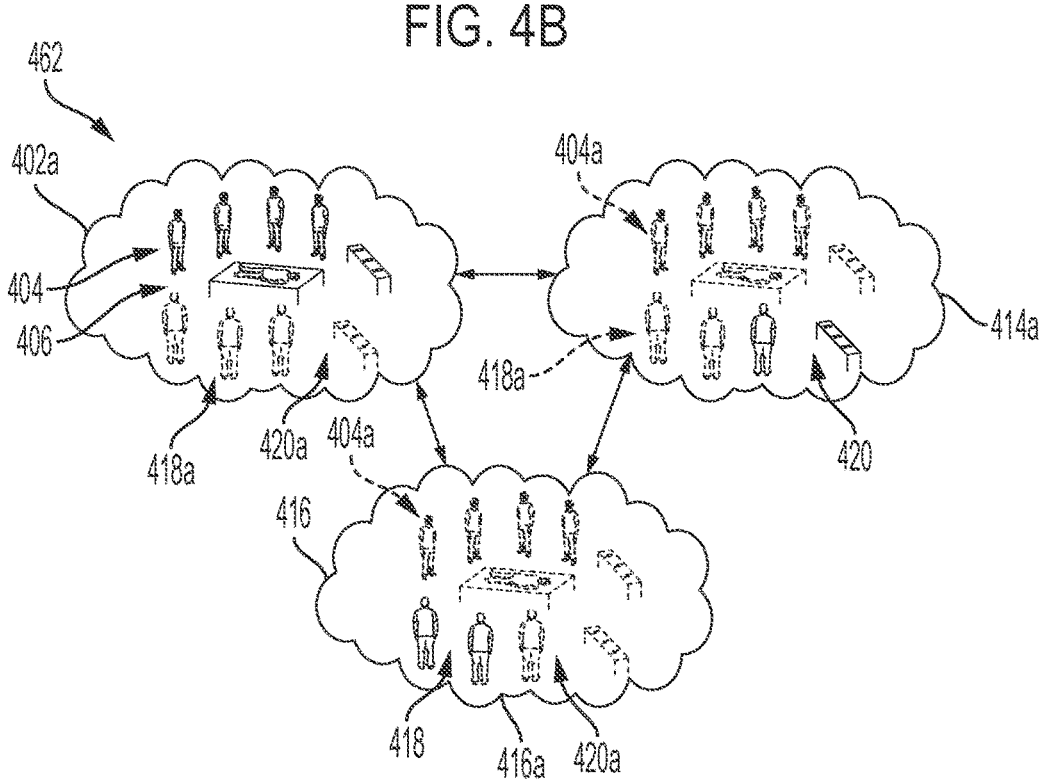

FIG. 4, including FIGS. 4A-4C, illustrates a medical procedure-based implementation example executed by system 100 of FIG. 1 for improving holographic image technology associated with generating interactive holographic image simulation replications for real time interactions with individuals, in accordance with embodiments of the present invention.

FIG. 4A illustrates an initial view of a primary location 402, a secondary location 414, and a secondary location 416. Primary location 402 includes a team of medical professionals 404 (e.g., doctors, nurses, etc.), a patient on an examination table 406, and a table comprising medical tools (objects) 420. Secondary location 414 comprises an expert doctor and table comprising medical tools 408. Secondary location 416 comprises expert doctors 418.

FIG. 4B illustrates a holographic representation 410 of all individuals and objects at primary location 402, secondary location 414, and secondary location 416. Holographic representation 410 includes a holographic representation 404a, a holographic representation 418a, and holographic representation 420a. Holographic representation 404a represents team of medical professionals 404, patient on an examination table 406, and table comprising medical tools (objects) 408 of FIG. 4A. Holographic representation 418a represents expert doctor and table comprising medical tools 408 of FIG. 4A. Holographic representation 420a represents expert doctors 418 of FIG. 4A.

FIG. 4C illustrates a subsequent view 462 of primary location 402, secondary location 414, and secondary location 416 holographic representation 410 of all individuals and objects at primary location 402, secondary location 414, and secondary location 416 of FIG. 4A. Subsequent view 462 illustrates virtualized: primary location 402a, secondary location 414a, and secondary location 416a. Primary location 402a includes team of medical professionals 404, patient on an examination table 406, table comprising medical tools (objects) 408, holographic representation 418a, and holographic representation 420a. Secondary location 414a includes expert doctor and table comprising medical tools 420, holographic representation 404a, and holographic representation 418a. Secondary location 416a comprises expert doctors 418, holographic representation 404a, and holographic representation 420a. Therefore, each of primary location 402a, secondary location 414a, and secondary location 416a includes real objects and holographic objects thereby presenting identical scenes for allowing each of the locations to work with each other as if they were all in the same location.

Figure 5:
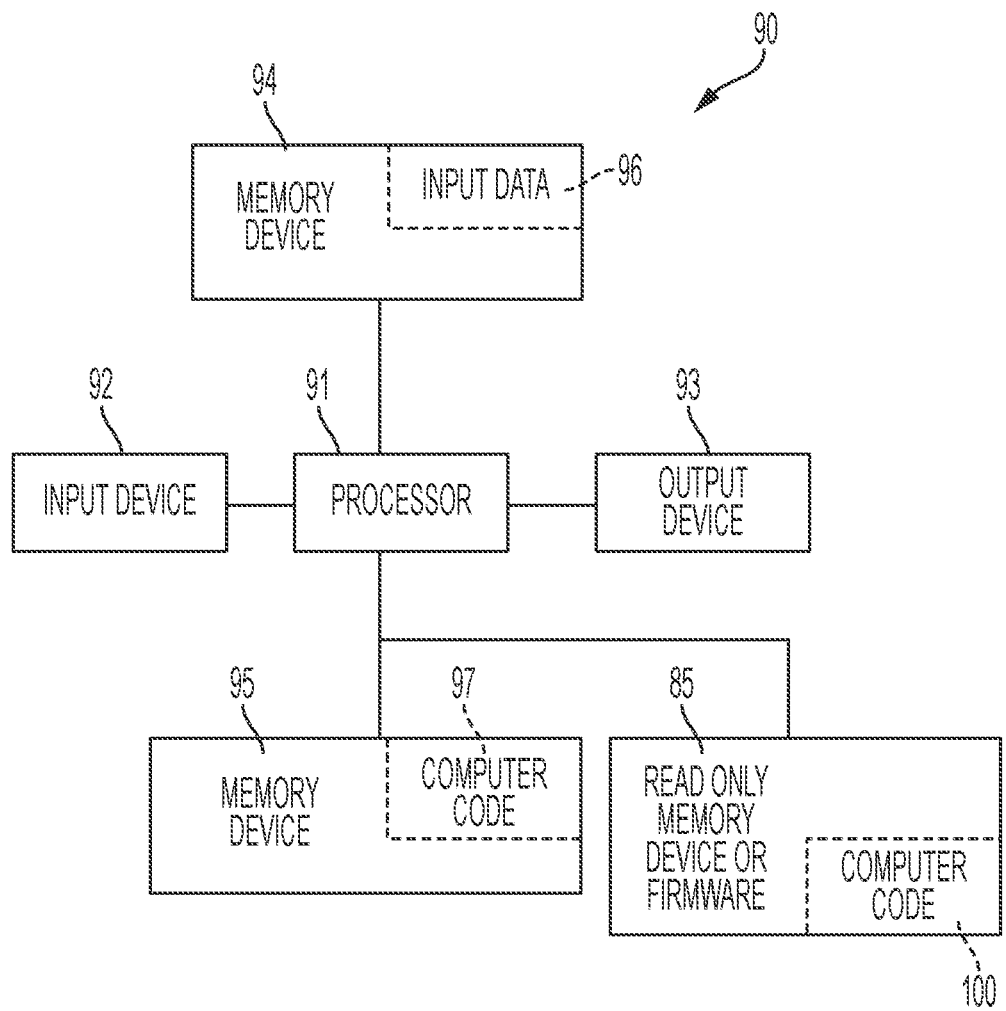
FIG. 5 illustrates a computer system used by the system of FIG. 1 for improving holographic image technology associated with generating interactive holographic image simulation replications for real time interactions with individuals, in accordance with embodiments of the present invention.

FIG. 5 illustrates a computer system 90 (e.g., holographic image hardware device 124, holographic projection device 114a . . . 114n, and database 108 of FIG. 1) used by or comprised by the system of FIG. 1 for improving holographic image technology associated with generating interactive holographic image simulation replications for real time interactions with individuals, in accordance with embodiments of the present invention.

Aspects of the present invention may take the form of an entirely hardware embodiment, an entirely software embodiment (including firmware, resident software, micro-code, etc.) or an embodiment combining software and hardware aspects that may all generally be referred to herein as a "circuit," "module," or "system."

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing apparatus receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, device (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing device to produce a machine, such that the instructions, which execute via the processor of the computer or other programmable data processing device, create means for implementing the functions/acts specified in the flowchart and/or block diagram block or blocks. These computer readable program instructions may also be stored in a computer readable storage medium that can direct a computer, a programmable data processing device, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing device, or other device to cause a series of operational steps to be performed on the computer, other programmable device or other device to produce a computer implemented process, such that the instructions which execute on the computer, other programmable device, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The computer system 90 illustrated in FIG. 4 includes a processor 91, an input device 92 coupled to the processor 91, an output device 93 coupled to the processor 91, and memory devices 94 and 95 each coupled to the processor 91. The input device 92 may be, inter alia, a keyboard, a mouse, a camera, a touchscreen, etc. The output device 93 may be, inter alia, a printer, a plotter, a computer screen, a magnetic tape, a removable hard disk, a floppy disk, etc. The memory devices 94 and 95 may be, inter alia, a hard disk, a floppy disk, a magnetic tape, an optical storage such as a compact disc (CD) or a digital video disc (DVD), a dynamic random-access memory (DRAM), a read-only memory (ROM), etc. The memory device 95 includes a computer code 97. The computer code 97 includes algorithms (e.g., the algorithm of FIG. 2) for improving holographic image technology associated with generating interactive holographic image simulation replications for real time interactions with individuals. The processor 91 executes the computer code 97. The memory device 94 includes input data 96. The input data 96 includes input required by the computer code 97. The output device 93 displays output from the computer code 97. Either or both memory devices 94 and 95 (or one or more additional memory devices Such as read only memory device 96) may include algorithms (e.g., the algorithm of FIG. 2) and may be used as a computer usable medium (or a computer readable medium or a program storage device) having a computer readable program code embodied therein and/or having other data stored therein, wherein the computer readable program code includes the computer code 97. Generally, a computer program product (or, alternatively, an article of manufacture) of the computer system 90 may include the computer usable medium (or the program storage device).

In some embodiments, rather than being stored and accessed from a hard drive, optical disc or other writeable, rewriteable, or removable hardware memory device 95, stored computer program code 84 (e.g., including algorithms) may be stored on a static, nonremovable, read-only storage medium such as a Read-Only Memory (ROM) device 85, or may be accessed by processor 91 directly from such a static, nonremovable, read-only medium 85. Similarly, in some embodiments, stored computer program code 97 may be stored as computer-readable firmware 85, or may be accessed by processor 91 directly from such firmware 85, rather than from a more dynamic or removable hardware data-storage device 95, such as a hard drive or optical disc.

Still yet, any of the components of the present invention could be created, integrated, hosted, maintained, deployed, managed, serviced, etc. by a service supplier who offers to improve holographic image technology associated with generating interactive holographic image simulation replications for real time interactions with individuals. Thus, the present invention discloses a process for deploying, creating, integrating, hosting, maintaining, and/or integrating computing infrastructure, including integrating computer-readable code into the computer system 90, wherein the code in combination with the computer system 90 is capable of performing a method for enabling a process for improving holographic image technology associated with generating interactive holographic image simulation replications for real time interactions with individuals. In another embodiment, the invention provides a business method that performs the process steps of the invention on a subscription, advertising, and/or fee basis. That is, a service supplier, such as a Solution Integrator, could offer to enable a process for improving holographic image technology associated with generating interactive holographic image simulation replications for real time interactions with individuals. In this case, the service supplier can create, maintain, support, etc. a computer infrastructure that performs the process steps of the invention for one or more customers. In return, the service supplier can receive payment from the customer(s) under a subscription and/or fee agreement and/or the service supplier can receive payment from the sale of advertising content to one or more third parties.

While FIG. 5 shows the computer system 90 as a configuration of hardware and software, any configuration of hardware and software, as would be known to a person of ordinary skill in the art, may be utilized for the purposes stated supra in conjunction with the computer system 90 of FIG. 5. For example, the memory devices 94 and 95 may be portions of a single memory device rather than separate memory devices.

Cloud Computing Environment

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 6:
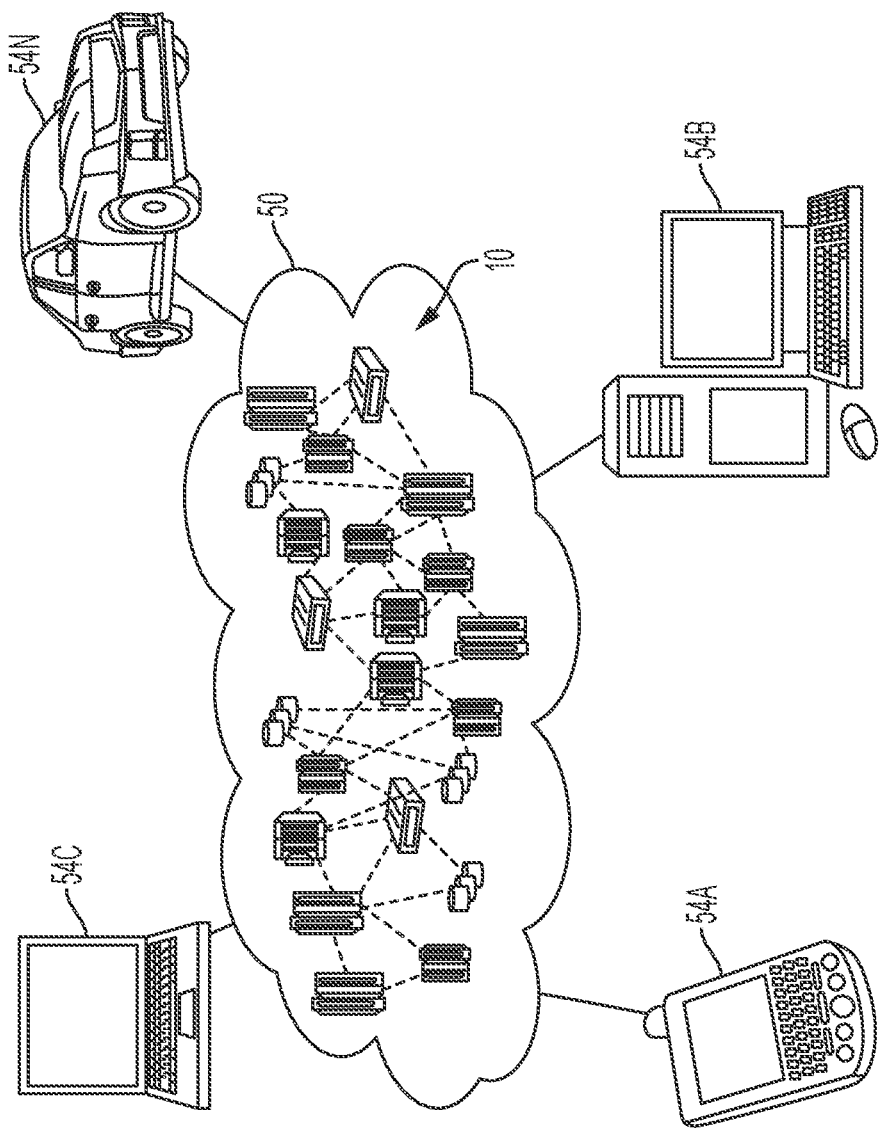
FIG. 6 illustrates a cloud computing environment, in accordance with embodiments of the present invention.

Referring now to FIG. 6, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A, 54B, 54C and 54N shown in FIG. 5 are intended to be illustrative only and that computing nodes 10 and cloud computing environment 50 can communicate with any type of computerized device over any type of network and/or network addressable connection (e.g., using a web browser).

Figure 7:
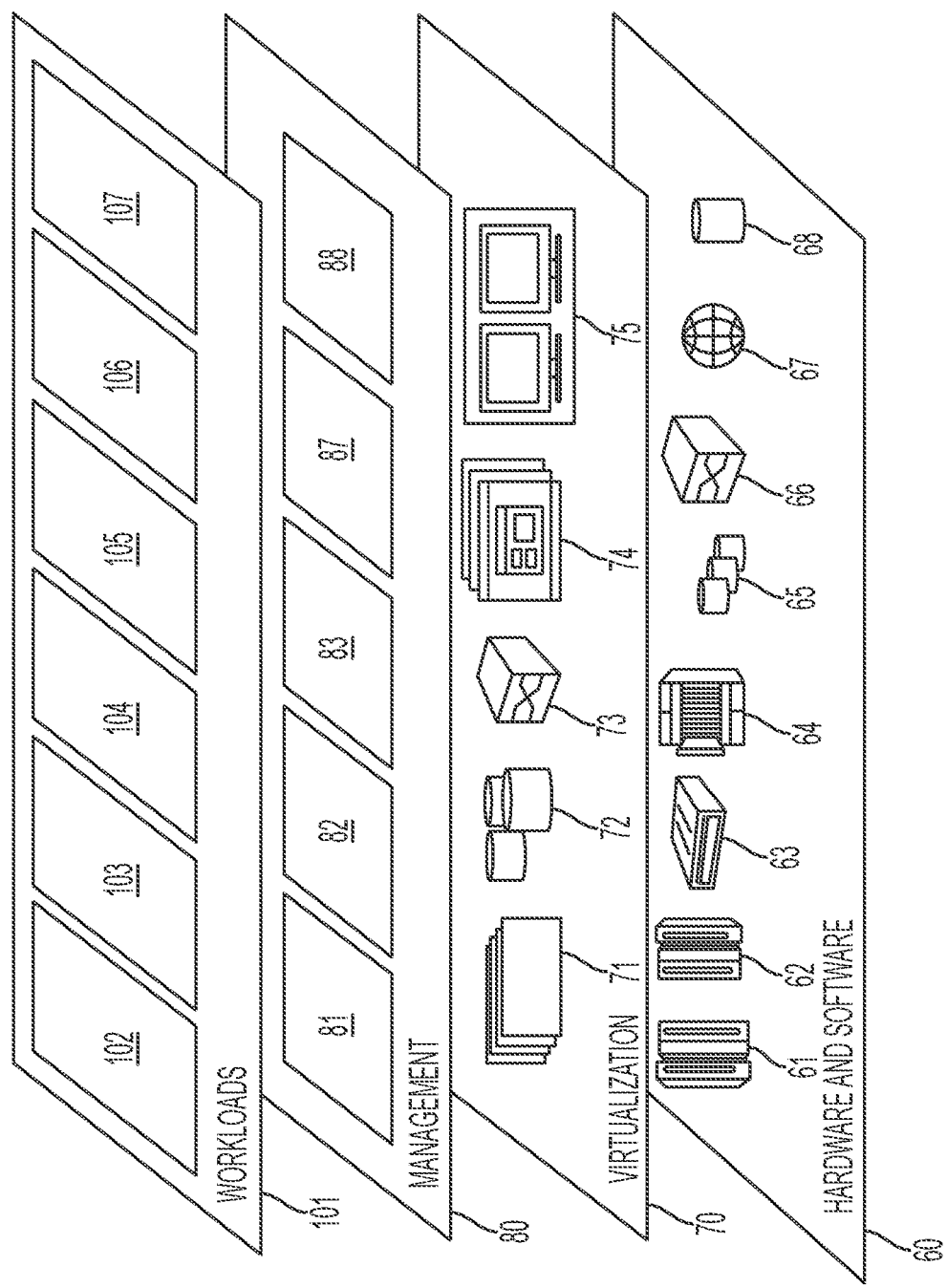
FIG. 7 illustrates a set of functional abstraction layers provided by cloud computing environment, in accordance with embodiments of the present invention.

Referring now to FIG. 7, a set of functional abstraction layers provided by cloud computing environment 50 (see FIG. 6) is shown. It should be understood in advance that the components, layers, and functions shown in FIG. 7 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 101 provides examples of functionality for which the cloud computing environment may be utilized. Examples of workloads and functions which may be provided from this layer include: mapping and navigation 102; software development and lifecycle management 103; virtual classroom education delivery 104; data analytics processing 105; transaction processing 106; and for improving holographic image technology associated with generating interactive holographic image simulation replications for real time interactions with individuals 108.

While embodiments of the present invention have been described herein for purposes of illustration, many modifications and changes will become apparent to those skilled in the art. Accordingly, the appended claims are intended to encompass all such modifications and changes as fall within the true spirit and scope of this invention.

What is claimed is:

1. A holographic image simulation and replication improvement method comprising:
   receiving, by a processor of a holographic image generation device, data identifying a primary location and at least one secondary location associated with a holographic replication event;
   continuously receiving in real time, by said processor via a plurality of sensors at said primary location, first video data describing first objects at said primary location, wherein said plurality of sensors comprise sensors selected from the group consisting of a video retrieval device, an audio retrieval device, a heatmap sensor, an optical sensor, and an ultrasonic sensor;
   continuously generating in real time, by said processor based on said first video data, a first holographic simulation presentation comprising virtual representations of said first objects with respect to said primary location;
   continuously receiving in real time, by said processor via a plurality of sensors at said at least one secondary location, second video data describing second objects at said at least one secondary location;
   continuously generating in real time, by said processor based on said second video data, a second holographic simulation presentation comprising virtual representations of said second objects with respect to said at least one secondary location;
   continuously projecting in real time, by said processor at said primary location, said second holographic simulation presentation such that said virtual representations of said second objects overlay and interact with said first objects at said primary location; and
   continuously projecting in real time, by said processor at said second location, said first holographic simulation presentation such that said virtual representations of said first objects overlay and interact with said second objects at said at least one secondary location.

2. The method of claim 1, wherein said continuously projecting said first holographic simulation presentation and said continuously projecting said second holographic simulation presentation occur simultaneously.

3. The method of claim 1, wherein said virtual representations of said first objects execute replicated virtual movements simultaneously with actual movements of said first objects, and wherein said virtual representations of said second objects execute replicated virtual movements simultaneously with actual movements of said second objects.

4. The method of claim 1, wherein said first video data describes a shape, a three-dimensional size, and a relative position of each of said first objects with respect to said primary location, and wherein said second video data describes a shape, a three-dimensional size, and a relative position of each of said second objects with respect to said at least one secondary location.

5. The method of claim 1, wherein said first objects comprise inanimate objects and living objects, and wherein said second objects comprise inanimate objects and living objects.

6. The method of claim 1, further comprising:
generating, by said processor based on said first holographic simulation presentation and said second holographic simulation presentation, self-learning software code for executing future holographic simulation presentations.

7. The method of claim 1, wherein said projecting said first holographic simulation presentation comprises projecting said virtual representations of said second objects interacting with said first objects at a speed that is equal to a real time speed of said second objects, and wherein said projecting said second holographic simulation presentation comprises projecting said virtual representations of said first objects interacting with said second objects at a speed that is equal to a real time speed of said first objects.

8. The method of claim 1, wherein said projecting said first holographic simulation presentation comprises projecting said virtual representations of said second objects interacting with said first objects at a speed that is less than a real time speed of said second objects, and wherein said projecting said second holographic simulation presentation comprises projecting said virtual representations of said first objects interacting with said second objects at a speed that is less than a real time speed of said first objects.

9. The method of claim 1, wherein said projecting said first holographic simulation presentation comprises projecting said virtual representations of said second objects interacting with said first objects at a speed that is greater than a real time speed of said second objects, and wherein said projecting said second holographic simulation presentation comprises projecting said virtual representations of said first objects interacting with said second objects at a speed that is greater than a real time speed of said first objects.

10. The method of claim 1, further comprising:
providing at least one support service for at least one of creating, integrating, hosting, maintaining, and deploying computer-readable code in the control hardware, said code being executed by the computer processor to implement: said receiving, said continuously receiving said first video data, said continuously generating said first holographic simulation, said continuously receiving said second video data, said continuously generating said second holographic simulation, said continuously projecting said second holographic simulation presentation, and said continuously projecting said first holographic simulation presentation.

11. A computer program product, comprising a computer readable hardware storage device storing a computer readable program code, said computer readable program code comprising an algorithm that when executed by a processor of a holographic image generation device implements a holographic image simulation and replication improvement method, said method comprising:
receiving, by said processor, data identifying a primary location and at least one secondary location associated with a holographic replication event;
continuously receiving in real time, by said processor via a plurality of sensors at said primary location, first video data describing first objects at said primary location, wherein said plurality of sensors comprise sensors selected from the group consisting of a video retrieval device, an audio retrieval device, a heatmap sensor, an optical sensor, and an ultrasonic sensor;
continuously generating in real time, by said processor based on said first video data, a first holographic simulation presentation comprising virtual representations of said first objects with respect to said primary location;
continuously receiving in real time, by said processor via a plurality of sensors at said at least one secondary location, second video data describing second objects at said at least one secondary location;
continuously generating in real time, by said processor based on said second video data, a second holographic simulation presentation comprising virtual representations of said second objects with respect to said at least one secondary location;
continuously projecting in real time, by said processor at said primary location, said second holographic simulation presentation such that said virtual representations of said second objects overlay and interact with said first objects at said primary location; and
continuously projecting in real time, by said processor at said second location, said first holographic simulation presentation such that said virtual representations of said first objects overlay and interact with said second objects at said at least one secondary location.

12. The computer program product of claim 11, wherein said continuously projecting said first holographic simulation presentation and said continuously projecting said second holographic simulation presentation occur simultaneously.

13. The computer program product of claim 11, wherein said virtual representations of said first objects execute replicated virtual movements simultaneously with actual movements of said first objects, and wherein said virtual representations of said second objects execute replicated virtual movements simultaneously with actual movements of said second objects.

14. The computer program product of claim 11, wherein said first video data describes a shape, a three dimensional size, and a relative position of each of said first objects with respect to said primary location, and wherein said second video data describes a shape, a three dimensional size, and a relative position of each of said second objects with respect to said at least one secondary location.

15. The computer program product of claim 11, wherein said first objects comprise inanimate objects and living objects, and wherein said second objects comprise inanimate objects and living objects.

16. The computer program product of claim 11, wherein said method further comprises:
generating, by said processor based on said first holographic simulation presentation and said second holographic simulation presentation, self-learning software code for executing future holographic simulation presentations.

17. The computer program product of claim 11, wherein said projecting said first holographic simulation presentation comprises projecting said virtual representations of said second objects interacting with said first objects at a speed that is equal to a real time speed of said second objects, and wherein said projecting said second holographic simulation presentation comprises projecting said virtual representations of said first objects interacting with said second objects at a speed that is equal to a real time speed of said first objects.

18. A holographic image generation device comprising a processor coupled to a computer-readable memory unit, said memory unit comprising instructions that when executed by the processor implements a holographic image simulation and replication improvement method comprising:
  receiving, by said processor, data identifying a primary location and at least one secondary location associated with a holographic replication event;
  continuously receiving in real time, by said processor via a plurality of sensors at said primary location, first video data describing first objects at said primary location, wherein said plurality of sensors comprise sensors selected from the group consisting of a video retrieval device, an audio retrieval device, a heatmap sensor, an optical sensor, and an ultrasonic sensor;
  continuously generating in real time, by said processor based on said first video data, a first holographic simulation presentation comprising virtual representations of said first objects with respect to said primary location;
  continuously receiving in real time, by said processor via a plurality of sensors at said at least one secondary location, second video data describing second objects at said at least one secondary location;
  continuously generating in real time, by said processor based on said second video data, a second holographic simulation presentation comprising virtual representations of said second objects with respect to said at least one secondary location;
  continuously projecting in real time, by said processor at said primary location, said second holographic simulation presentation such that said virtual representations of said second objects overlay and interact with said first objects at said primary location; and
  continuously projecting in real time, by said processor at said second location, said first holographic simulation presentation such that said virtual representations of said first objects overlay and interact with said second objects at said at least one secondary location.

* * * * *